(12) United States Patent
Ichihara et al.

(10) Patent No.: US 9,187,443 B2
(45) Date of Patent: Nov. 17, 2015

(54) METHOD FOR PRODUCING EPOXY COMPOUND

(71) Applicants: JX Nippon Oil & Energy Corporation, Tokyo (JP); OSAKA UNIVERSITY, Suita-shi, Osaka (JP)

(72) Inventors: Junko Ichihara, Suita (JP); Shunro Yamaguchi, Suita (JP); Atsushi Kameyama, Tokyo (JP); Takashi Suzuki, Tokyo (JP); Takashi Morikita, Tokyo (JP)

(73) Assignees: JX Nippon Oil & Energy Corporation, Tokyo (JP); OSAKA UNIVERSITY, Suita-shi, Osaka (JP)

( * ) Notice: Subject to any disclaimer, the term of this patent is extended or adjusted under 35 U.S.C. 154(b) by 0 days.

(21) Appl. No.: 14/402,481

(22) PCT Filed: Apr. 26, 2013

(86) PCT No.: PCT/JP2013/062357
§ 371 (c)(1),
(2) Date: Nov. 20, 2014

(87) PCT Pub. No.: WO2013/175938
PCT Pub. Date: Nov. 28, 2013

(65) Prior Publication Data
US 2015/0141677 A1   May 21, 2015

(30) Foreign Application Priority Data
May 22, 2012  (JP) .................. 2012-116391

(51) Int. Cl.
*C07D 303/00* (2006.01)
*C07D 301/12* (2006.01)
*C07D 493/04* (2006.01)

(52) U.S. Cl.
CPC ............ *C07D 301/12* (2013.01); *C07D 493/04* (2013.01)

(58) Field of Classification Search
CPC ..... C07D 493/04; C07D 301/12; B01J 23/30; B01J 31/34
USPC ........................................ 549/544
See application file for complete search history.

(56) References Cited

U.S. PATENT DOCUMENTS 5,430,161 A * 7/1995 Brown et al. ................. 549/531
2010/0113807 A1   5/2010 Ichihara et al.

FOREIGN PATENT DOCUMENTS

JP    S62-234550 A    10/1987
JP    2010-235649 A   10/2010
WO    2008093711 A1    8/2008

OTHER PUBLICATIONS

Okovytyy et al, "Identification of the stereoisomers of tetrahydroindene diepoxide by the 1H and 13C NMR characteristics: A combined experimental and theoretical study," Journal of Molecular Structure: THEOCHEM, vol. 730, No. 1-3, pp. 125-132 (2005).
Matoba et al, "Epoxidation of cyxlic diolefins with hydrogen peroxide catalyzed by areneseleninic acid," Journal of Japan Petroleum Institute, vol. 26, No. 5, pp. 349-354 (1983).
Int'l Search Report issued Jun. 11, 2013 in Int'l Application No. PCT/JP2013/062357.

* cited by examiner

*Primary Examiner* — T. Victor Oh
(74) *Attorney, Agent, or Firm* — Panitch Schwarze Belisario & Nadel LLP

(57) ABSTRACT

A method is provided for carrying out epoxidation of an olefin compound with good productivity. The method produces an epoxy compound by reacting a compound having a carbon-carbon double bond with hydrogen peroxide by carrying out repeatedly or continuously the following steps: (1) reacting a compound having a carbon-carbon double bond with hydrogen peroxide in the coexistence of (a) the compound having a carbon-carbon double bond, (b) a hydrogen peroxide solution, (c) a powdered solid catalyst support, and (d) a powdered solid catalyst, and optionally further (e) an organic solvent to produce an epoxy compound; (2) separating the epoxy compound reaction product from the reaction mixture produced in (1); and (3) adding (d) and also adding (a), (b), (c), and optionally further (e) to the mixture of the powdered solid catalyst support and powdered solid catalyst after separating the reaction product in (2).

10 Claims, No Drawings

METHOD FOR PRODUCING EPOXY COMPOUND

CROSS-REFERENCE TO RELATED APPLICATION

This application is a Section 371 of International Application No. PCT/JP2013/062357, filed Apr. 26, 2013, which was published in the Japanese language on Nov. 28, 2013, under International Publication No. WO 2013/175938 A1, and the disclosure of which is incorporated herein by reference.

TECHNICAL FIELD

The present invention relates to a method for producing an epoxy compound from an olefin compound and hydrogen peroxide.

BACKGROUND ART

Epoxy compounds are reacted with various curing agents and curing catalysts to produce cured products. These epoxy compounds are useful as components of coating agents, adhesives, inks or sealants or intermediates for producing compounds which are useful in the various final applications such as pharmaceutical agents or medical products.

As a method for producing an epoxy compound, a method is known, in which olefins are oxidized with peracids such as peracetic acid. However, this method has problems that peracids require careful handling, and epoxides are reacted with carboxylic acids present in the reaction system thereby producing esters and the like, resulting in a decrease in the selectivity of the epoxides and that the post-treatments are troublesome. Therefore, a method has been attracting attention, which uses hydrogen peroxide as an oxidation agent, which is easy in handling and turns to water that is harmless after the reaction.

As a method for producing an epoxy compound from olefins using hydrogen peroxide, a method is known in which epoxidation is carried out by reacting olefins and a hydrogen peroxide solution with a halogenated hydrocarbon as a solvent using a catalyst such as polyacids (Patent Literature 1). This method, however, has problems concerning halogen impurities in the products and environmental load due to the use of the halogenated hydrocarbon.

Patent Literature 2 discloses a solid phase reaction system for oxidation comprising a mixture of a powdered solid catalyst support and a powdered solid catalyst for oxidation reaction, an organic compound and a hydrogen peroxide solution.

CITATION LIST

Patent Literature

Patent Literature 1: Japanese Patent Application Laid-Open Publication No. 62-234550
Patent Literature 2: WO2008/093711

SUMMARY OF INVENTION

Technical Problem

The present invention has an object to provide a method for carrying out epoxidation of an olefin compound with good productivity.

Solution to Problem

The present invention relates to a method for producing an epoxy compound by reacting a compound having a carbon-carbon double bond with hydrogen peroxide, comprising carrying out repeatedly or continuously the following steps (1), (2) and (3):

step (1) of reacting a compound having a carbon-carbon double bond with hydrogen peroxide in the coexistence of (a) the compound having a carbon-carbon double bond, (b) a hydrogen peroxide solution, (c) a powdered solid catalyst support and (d) a powdered solid catalyst and optionally further (e) an organic solvent to produce an epoxy compound;

step (2) of separating the epoxy compound that is the reaction product from the reaction mixture produced in step 1; and step (3) of adding (d) the powdered solid catalyst and also adding (a) the compound having a carbon-carbon double bond, (b) the hydrogen peroxide solution, (c) the powdered solid catalyst support and optionally further (e) the organic solvent to the mixture of the powdered solid catalyst support and powdered solid catalyst after separating the reaction product in step (2).

The present invention also relates to the foregoing method for producing an epoxy compound wherein the amount of the solid powdered catalyst added in step (3) is 1 percent by mass or more and 20 percent by mass or less on the basis of the mass of the compound having a carbon-carbon double bond added in step (3).

The present invention also relates to the foregoing method for producing an epoxy compound wherein the total mass of the powdered solid catalyst and the powdered solid catalyst support is 100 percent by mass or less on the basis of the total mass of the compound having a carbon-carbon double bond and the hydrogen peroxide solution.

The present invention also relates to the foregoing method for producing an epoxy compound wherein the organic solvent is selected from the group consisting of aliphatic hydrocarbons, aromatic hydrocarbons, alcohols, ethers, esters, amides, ketones, nitriles, sulfones, epoxides and mixtures thereof.

The present invention also relates to the foregoing method for producing an epoxy compound wherein the amount of the organic solvent is from 0 to 500 percent by mass on the basis of the compound having a carbon-carbon double bond.

The present invention also relates to the foregoing method for producing an epoxy compound wherein the solid catalyst is selected from the group consisting of: oxides of metals selected from the group consisting of tungsten, molybdenum and vanadium; oxoacids containing metals selected from the group consisting of tungsten, molybdenum and vanadium and salts thereof; and oxides, halides and sulfates of elements selected from the group consisting of iron, manganese and ruthenium.

The present invention also relates to the foregoing method for producing an epoxy compound wherein the solid catalyst is selected from the group consisting of oxides of tungsten or molybdenum, isopolyacids containing tungsten or molybdenum and heteropolyacids containing tungsten or molybdenum and particularly relates to the foregoing method for producing an epoxy compound wherein the solid catalyst is an isopolyacid containing tungsten.

The present invention also relates to the foregoing method for producing an epoxy compound wherein the solid catalyst support is selected from the group consisting of phosphates, diatomaceous earth, silica, alumina, kaolin, silica-alumina and calcium fluoride and particularly relates to the foregoing method for producing an epoxy compound wherein the solid catalyst support is apatite.

Advantageous Effect of Invention

The method for producing an epoxy compound of the present invention has features that it can produce an epoxy compound from a compound having carbon-carbon double bond at a higher reaction rate and yield and the resulting product is easily isolated and recovered. Furthermore, the method can reuse the solid catalyst and solid catalyst support only by adding a small amount of the solid catalyst after separation of the product and has advantages of stable product quality, safe operation in production facilities and reductions in environmental loads caused by treatment of waste material and waste water.

DESCRIPTION OF EMBODIMENTS

Preferable embodiments of the present invention will be described below.

The method for producing an epoxy compound of the present invention is a method for producing an epoxy compound by reacting a compound having a carbon-carbon double bond with hydrogen peroxide, comprising carrying out repeatedly the following steps (1), (2) and (3):

step (1) of reacting a compound having a carbon-carbon double bond with hydrogen peroxide in the coexistence of (a) the compound having a carbon-carbon double bond, (b) a hydrogen peroxide solution, (c) a powdered solid catalyst support and (d) a powdered solid catalyst and optionally further (e) an organic solvent to produce an epoxy compound;

step (2) of separating the epoxy compound that is the reaction product from the reaction mixture produced in step 1; and step (3) of adding (d) the powdered solid catalyst and also adding (a) the compound having a carbon-carbon double bond, (b) the hydrogen peroxide solution, (c) the powdered solid catalyst support and optionally further (e) the organic solvent to the mixture of the powdered solid catalyst support and powdered solid catalyst after separating the reaction product in step (2).

Since the method of the present invention does not use peracid unlike methods as disclosed in Patent Literature 1, no carboxylic acid is present in the system and as the result the method can suppress the production of esters and alcohols and thus is higher in epoxidation selectivity. Although there is a problem that in production of an alicyclic epoxy compound, particularly an alicyclic diepoxy compound regarded as having a high reactivity with acids, coexisting organic acids are easily reacted with epoxy groups produced in the presence of water, resulting in a decrease in the selectivity of the epoxides due to the ring-opening of the epoxy groups, the present invention can achieve a higher epoxidation selectivity for such compounds.

To the mixture of the powdered solid catalyst support and the powdered solid catalyst after separating the reaction product in step (2) are added (d) a powdered solid catalyst and also the raw materials that are (a) a compound having a carbon-carbon double bond and (b) a hydrogen peroxide solution and optionally further (e) an organic solvent in step (3), and then the resulting mixture is returned to step (1) so that an epoxy compound can be produced repeatedly or continuously while the solid catalyst support and solid catalyst are reused, resulting in achievement of the product quality stability, safe operation in production facilities and reductions in production cost and environmental loads.

No particular limitation is imposed on the compound having a carbon-carbon double bond used in the present invention if it is a compound having one or more carbon-carbon double bonds per molecule.

Examples of such a compound include monosubstituted olefins such as ethylene, propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl)styrene, allylbenzene, 4-methoxystyrene, safrole, eugenol, and 3,4-dimethoxy-1-allylbenzene;

disubstituted olefins such as 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methylcyclohexene, cycloheptene, cyclooctene, cyclodecene, cyclododecene, methylenecyclohexane, β-methylstyrene, stilbene, isosafrole, isoeugenol, β-pinene and norbornene;

trisubstituted olefins such as 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)cyclohexene, 1-isopropylcyclohexene, 2-carene, 3-carene and α-pinene; and tetrasubstituted olefins such as 2,3-dimethyl-2-butene and 2,3,4-trimethyl-2-pentene.

Alternatively, in the present invention, other than the above-described olefin compounds, alicyclic olefin compounds represented by formula (2) below are also preferably used:

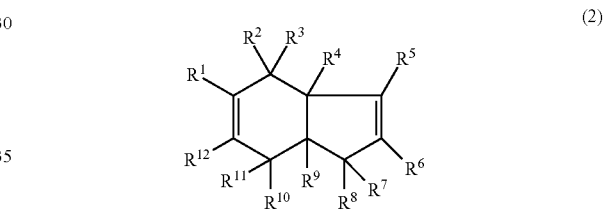

(2)

In formula (2), $R^1$, $R^2$, $R^3$, $R^4$, $R^5$, $R^6$, $R^7$, $R^8$, $R^9$, $R^{10}$, $R^{11}$ and $R^{12}$ are each independently hydrogen, halogen, an alkyl group which may have a substituent or an alkoxy group which may have a substituent.

The alkyl group is preferably an alkyl group having 1 to 10 carbon atoms, more preferably an alkyl group having 1 to 4 carbon atoms. When the alkyl group has a substituent, examples thereof include halogens and alkoxy groups.

The alkoxy group is preferably an alkoxy group having 1 to 10 carbon atoms, more preferably an alkoxy group having 1 to 4 carbon atoms. When the alkoxy group has a substituent, examples thereof include halogens and alkoxy groups.

$R^1$ to $R^{12}$ are each independently preferably, hydrogen, fluorine, an alkyl group or an alkoxy group, more preferably hydrogen or fluorine, more preferably hydrogen.

That is, the alicyclic olefin compound represented by formula (2) is preferably a compound represented by formula (3) below from which an alicyclic diepoxy compound represented by formula (1) below can be produced through oxidation reaction.

(3)

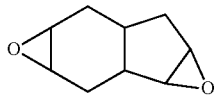
(1)

The solid catalyst support may be powders of solid materials having properties that they disperse a solid catalyst, a hydrogen peroxide solution and a compound having a carbon-carbon double bond, are not degraded thereby and do not disturb the oxidation reaction, preferably those having properties to facilitate the oxidation reaction. Specific examples include phosphates such as apatite, clays such as diatomaceous earth [main component: silica], kaolin [main component: silica-alumina] and hydrotalcite, fluorides such as calcium fluoride, and oxides such as silica, titania and alumina. Among these, a solid catalyst support selected from phosphates, diatomaceous earth, silica, alumina, kaolin, silica-alumina and calcium fluoride is preferably used because they can achieve a higher yield. In particular, a solid catalyst support selected from apatite, diatomaceous earth and calcium fluoride can achieve a particularly higher yield.

Herein, the apatite is a kind of calcium phosphate, and fluorapatite, chlorapatite, carbonate apatite and hydroxyapatite exist as apatite-type minerals. Among these, hydroxyapatite and fluorapatite are preferably used.

The diatomaceous earth is a soft rock or soil composed mainly of a husk of Bacillariophyta, and contains silica as a main component but also often alumina, ferric oxide, alkali metal oxides in addition to silica. Alternatively, those which are porous and have a high porosity and a cake bulk density of about 0.2 to 0.45 are often used. Among diatomaceous earths, calcined products or freshwater diatomaceous earths are preferred but other diatomaceous earths may be used. Specific examples of such diatomaceous earths include those marketed under the tradename of Celite (registered trademark) by Celite Corporation and marketed under the tradename of Celatom by Eagle Pitcher Minerals, Inc. Alternatively, those calcined together with sodium carbonate may also be used.

Examples of the solid catalyst include: oxides of metals selected from the group consisting of tungsten, molybdenum and vanadium; oxoacids containing metals selected from the group consisting of tungsten, molybdenum and vanadium and salts thereof; and oxides, halide and sulfates of elements selected from the group consisting of iron, manganese and ruthenium.

Examples of the oxides of metals selected from the group consisting of tungsten, molybdenum and vanadium include $WO_3$, $MoO_3$ and $V_2O_5$. Examples of the oxoacids containing metals selected from the group consisting of tungsten, molybdenum and vanadium and salts thereof include tungstic acid ($H_2WO_4$) and tungstates such as $Na_2WO_4$, molybdenum acid ($H_2MoO_4$) and molybdates such as $Na_2MoO_4$, vanadic acid and vanadates such as $NH_4VO_3$, isopolyacids containing tungsten, molybdenum or vanadium and salts thereof, and heteropolyacids containing tungsten, molybdenum or vanadium and salts thereof. Isopolyacids or heteropolyacids containing tungsten, molybdenum or vanadium also include mixtures represented by $Q_3[PW_6Mo_6O_{40}]$ and $Q_7[PV_4Mo_8O_{40}]$ and peroxo-type compounds represented by $Q_3\{PO_4[W(O)(O_2)]_4\}$ and $Q_2[W_2O_3(O_2)_4]$ (in these formulae, Q represents a counter cation).

Examples of the hetero atom of the heteropolyacids include phosphorus, boron, silicone, germanium, lanthanoid elements, manganese, nickel, iron, cobalt or ruthenium. Examples of the counter cations of the isopolyacid salts or heteropolyacid salts include organic cations such as tetrabutylammonium, butylammonium, benzyltrimethylammonium, cetyltrimethylammonium and cetylpyridinium and inorganic cations such as ammonium, potassium, sodium and calcium.

More specifically, examples of the isopolytungstic acids containing tungsten include $(NH_4)_6W_7O_{24}$, $(NH_4)_{10}[H_2W_{12}O_{42}]$, $(CetylNMe_3)_7(NH_4)_3[H_2W_{12}O_{42}]$, $(CetylNMe_3)_{10}[H_2W_{12}O_{42}]$, $(CetylPy)_9(NH_4)[H_2W_{12}O_{42}]$, $(CetylPy)_{10}[H_2W_{12}O_{42}]$, $(CetylPy)_4[W_{10}O_{32}]$ and $K_4[W_{10}O_{32}]$, and examples of the heteropolytungstic acids containing tungsten include $(CetylPy)_3[PW_{12}O_{40}]$, $(CetylPy)_5H_2[PW_{11}O_{39}]$ and $Na_9[PW_9O_{34}]$ and also those produced by replacing phosphorus (P) in the above-described heteropolytungstic acids with boron (B), silicon (Si) or germanium (Ge). $CetylNMe_3$ and $CetylPy$ in the formulae represent cetyltrimethylammonium and cetylpyridinium, respectively.

Examples of the oxoacid containing molybdenum and salts thereof include compounds produced by replacing tungsten in the compounds exemplified above as oxoacid containing tungsten and salts thereof, with molybdenum. Examples of the oxoacid containing vanadium and salts thereof include compounds produced by replacing tungsten in the compounds exemplified above as the oxoacid containing tungsten and salts thereof, with vanadium.

Among these solid catalysts, preferred are catalysts selected from the group consisting of oxides of tungsten or molybdenum, isopolyacids containing tungsten or molybdenum and heteropolyacids containing tungsten or molybdenum and particularly preferred are catalysts selected from the group consisting of isopolyacids and heteropolyacids containing tungsten because a higher selectivity can be achieved with these catalysts.

Examples of the oxides, halides or sulfates of elements selected from the group consisting of iron, manganese and ruthenium include $FeCl_3$, $MnSO_4$ and $RuCl_3$.

The solid catalyst is not required to be immobilized to the solid catalyst support, and all what needs to be done is that the powdered solid catalyst is simply mixed with the powdered solid catalyst support. For example, the powdered solid catalyst is added in advance to the powdered solid catalyst support and then stirred and mixed thereby producing a mixture of the solid catalyst and solid catalyst support. No particular limitation is imposed on the particle sizes of the powdered solid catalyst and powdered solid catalyst support. Those having a particle size of about 5 to 100 μm, which are easily available may be used thereby achieving the advantageous effects of the present invention such as a higher yield of the product.

The amount of the solid catalyst is preferably 5 to 60 percent by mass, more preferably 10 to 50 percent by mass on the basis of the amount of the solid catalyst support. With 5 percent by mass or less of the catalyst, the compound represented by formula (1) cannot be produced at a high yield because the reaction rate is decreased. With more than 60 percent by mass of the catalyst, the yield cannot be improved, and thus it is industrially disadvantageous.

In step (1) of the method of the present invention, an epoxy compound is produced by mixing (a) a compound having a carbon-carbon double bond to be oxidized and (b) a hydrogen peroxide solution and optionally (e) an organic solvent with a mixture of (c) a powdered solid catalyst support and (d) a powdered solid catalyst to react (a) the carbon-carbon double bond with hydrogen peroxide in the coexistence of (a) to (e).

The hydrogen peroxide solution may be used in an amount of about 0.5 to 5 mmol as hydrogen peroxide on the basis of 1 mmol of the double bond site of (a), but the amount is desirously from 0.6 to 2.5 mmol. Less than 0.5 mmol of the hydrogen peroxide solution results in lack of hydrogen peroxide and thus in a decrease in the yield of the epoxy compound while more than 5 mmol of the hydrogen peroxide solution results in a decrease in the concentration of (a) and thus in a failure to produce the epoxy compound with good productivity.

The solid catalyst support and solid catalyst may be used in an amount of about 0.01 to 0.4 g on the basis of 1 mmol of (a) but desirously 0.05 to 0.2 g.

In the present invention, the hydrogen peroxide solution is used at a concentration of preferably 5 to 60 percent by mass, more preferably 5 to 35 percent by mass. In the case of using a hydrogen peroxide solution of a low concentration in a method for producing an epoxy compound using hydrogen peroxide, the produced epoxide is hydrolyzed to produce by-products such as diols and the like, resulting in the reduced selectivity of the intended product. However, the method of the present invention is high in selectivity and can produce the intended product at a higher yield even in the case of using a hydrogen peroxide solution of low concentration.

Preferably in step (1) of the method of the present invention, the mixture of (c) a powdered solid catalyst support and (d) a powdered solid catalyst is mixed with (a) a compound having a carbon-carbon double bond and (b) a hydrogen peroxide solution and optionally further (e) an organic solvent to be formed into a slurry, in which the components are dispersed and contact with one another to oxidize the compound having a carbon-carbon double bond thereby producing an epoxy compound. In the present invention the oxidation reaction is carried out while the components are each dispersed in the slurry and contact with one another. As the result, the method of the present invention can produce epoxides at a higher productivity comparing with a reaction carried out in a solid phase and also can easily remove the reaction heat and thus improve the safety.

In order to form a proper slurry, it is desired to adjust the ratio of the solid powders and the organic solutions to a specific mass ratio. The total charge mass of (c) a powdered solid catalyst support and (d) a powdered solid catalyst for forming a slurry is 100 percent by mass or less, preferably within the range of 10 to 100 percent by mass on the basis of the total charge mass of (a) a compound having a carbon-carbon double bond, (b) a hydrogen peroxide solution and (e) an organic solvent. If the mass ratio is more than 100 percent by mass, a slurry may not be formed. If the mass ratio is less than 10 percent by mass, the reaction rate is reduced and thus the yield of an epoxy compound would be decreased.

The amount of the organic solvent to be used for forming a slurry is from 0 to 500 percent by mass, preferably 0 to 200 percent by mass on the basis of the mass of the compound having a carbon-carbon double bond. If the mass ratio exceeds 500 percent by mass, the productivity of an epoxy compound cannot be improved because the concentration of (a) would be reduced.

No particular limitation is imposed on (e) the organic solvent used in the present invention. Examples of the organic solvent include aliphatic hydrocarbons, aromatic hydrocarbons, alcohols, ethers, esters, amides, ketones, nitrile, sulfones, epoxides, and mixtures thereof. The organic solvent is preferably ethanol, ethyl acetate, hexane or toluene, more preferably toluene.

In the present invention, the oxidation reaction mode is not limited to a batch mode or a continuous mode but is preferably a batch mode. No particular limitation is imposed on the addition order of (a) to (e). The reaction may be carried out by adding (c) and (d) to (a) and (e) to form a slurry and then adding thereto dropwise (b). For the reaction in the present invention, it is important to suppress particles from settling and keep the contact efficiency of oil and water. The reaction is usually carried out stirring.

In the present invention, the oxidation reaction temperature is generally preferably from 0 to 50° C., more preferably 5 to 40° C. At lower than 0° C., the reaction proceeds slowly while at higher than 50° C., it causes the yield to decrease due to deactivation of the solid catalyst or ring-opening of the epoxides.

The reaction time is generally preferably from 1 to 24 hours, more preferably 1 to 12 hours. With a reaction time of shorter than 1 hour, the reaction does not proceed sufficiently and thus decreases the yield while with a reaction time of longer than 24 hours, the productivity decreases.

In step (2) of the method of the present invention, an epoxy compound that is the reaction product is separated from the reaction mixture (the mixture containing (a) to (e) and the reaction product after the reaction) produced in step (1) above.

No particular limitation is imposed on the method for separating the reaction product. Examples of the method include filtration, centrifugal separation and solvent extraction. The separated solid phase may be washed with water or an organic solvent. In general, a method is simple and advantageous, in which a mixture of (a) to (e) and the reaction product after the reaction is filtered and the residue (a mixture containing mainly the powdered solid catalyst support and powdered solid catalyst) is washed with an organic solvent.

In the present invention, the conversion rate of (a) the compound having a carbon-carbon double bond is preferably 50% or greater, and the yield of an epoxy compound is preferably 30% or greater.

The chlorine content of the epoxy compound produced by the present invention is preferably 100 ppm by mass or less, more preferably 10 ppm by mass or less because the compound when formed into a cured resin product can be further improved in moisture proof reliability. The chlorine content is the value measured in accordance with JIS K-7243-3, specifically the value measured by dissolving a sample (an epoxy compound) in diethylene glycol monobutyl ether and saponifying the solution with a potassium hydroxide alcohol solution, heating it to reflux, followed by potentiometric titration with a silver nitrate solution.

The chlorine content of the epoxy compound can be reduced by purification by distillation, or alternatively by a method such as alkali aqueous solution washing or absorbent treatment.

The metal content of the epoxy compound produced by the present invention is preferably 100 ppm by mass or less, more preferably 10 ppm by mass or less because a cured resin product produced from the compound is further enhanced in mechanical characteristics and electrical characteristics. The metal content can be measured by analyzing a 10% toluene solution of a sample (an epoxy compound) with inductively-coupled plasma emission (ICP emission). The apparatus for the measurement may be Optima 4300DV manufactured by Perkin-Elmer Corp. In this measurement, quantitative analysis of each metal species detected by qualitative analysis can be carried out using a commercially available metal standard solution.

The metal content of the epoxy compound can be reduced by purification by distillation, or alternatively by a method such as alkali aqueous solution washing or absorbent treatment.

In step (3) of the method of the present invention, to the mixture of the powdered solid catalyst support and the powdered solid catalyst after separating the reaction product in step (2) are added (d) a powdered solid catalyst and also (a) a compound having a carbon-carbon double bond and (b) a hydrogen peroxide solution and if necessary further (e) an organic solvent used as the raw materials for oxidation reaction in step (1). In step (3), (c) a powdered solid catalyst support may be added if necessary.

No particular limitation is imposed on the addition order of (d) the powdered solid catalyst and the raw materials (a), (b) and (e). For example, to the mixture of the powdered solid catalyst support and powdered solid catalyst after separating the reaction product in step (2) may be added (d), (a), (b) and (e) at the same time, alternatively (a), (b) and (e) after addition of (d), of further alternatively (d) after addition of (a), (b) and (e). In general, (d) is preferably added after addition of (a), (b) and (e) because a slurry can be easily formed.

In step (3), (a), (b) and (e) are each added in their corresponding amounts in which they have been added in step (1).

The amount of the powdered solid catalyst added in step (3) is preferably 1 percent by mass or more and 20 percent by mass or less, more preferably 2 percent by mass or more 14 percent by mass or less on the basis of the mass of (a) the compound having a carbon-carbon double bond added in step (3). If the amount is less than 1 percent by mass, the activity would be low. If the amount exceeds 20 percent by mass, it would be difficult to form a slurry.

In step (3) of the method of the present invention, to the mixture of the powdered solid catalyst support and the powdered solid catalyst after separating the reaction product in step (2) are added (d) a powdered solid catalyst and also the raw materials that are (a) a compound having a carbon-carbon double bond and (b) a hydrogen peroxide solution and optionally further (e) an organic solvent and the resulting mixture is returned to step (1) to repeat steps (1) to (3) so that an epoxy compound can be produced repeatedly.

EXAMPLES

The present invention will be described in more detail with the following examples but is not limited thereto.

Example 1

Into a screw-top test tube were weighed out 0.50 g of apatite that is a solid catalyst support and 0.085 g (0.015 mmol) of $(Cety1Py)_9(NH_4)[H_2W_{12}O_{42}]$ that is a solid catalyst, followed by well-mixing. To the mixture were added 0.60 g (5.0 mmol) of tetrahydroindene and 0.87 g (9.0 mmol) of a 35% hydrogen peroxide. After the mixture was stirred at 20° C. for 6 hours, the resulting reaction mixture was extracted with toluene (1 mL×3 times). The solvent was distilled out from the extracted solution thereby producing a crude product. The crude product was fed into a distillation still and distilled at a pressure of 2 mmHg thereby producing 0.43 g of tetrahydroindene diepoxide as a fraction at a column top temperature of 90° C. The yield of the product (diepoxide yield) was 57%. As the residue resulting from the extraction, 0.56 g of a solid catalyst support and solid catalyst mixture was produced.

$(Cety1Py)_9(NH_4)[H_2W_{12}O_{42}]$ that is a solid catalyst was weighed out in an amount of 0.028 g (0.0050 mmol) and then well-mixed with 0.56 g of the extract residue. To the mixture were added 0.60 g (5.0 mmol) of tetrahydroindene and 0.87 g (9.0 mmol) of a 35% hydrogen peroxide solution. After the mixture was stirred at 20° C. for 6 hours, the reaction mixture was extracted with toluene (1 mL×3 times). The solvent was distilled out from the extracted solution thereby producing a crude product. The crude product was fed into a distillation still and distilled at a pressure of 2 mmHg thereby producing 0.43 g of tetrahydroindene diepoxide as a fraction at a column top temperature of 90° C. The yield of the product (diepoxide yield) was 57%. Repeated use of the extract residue that is a solid catalyst support and solid catalyst mixture in the same manner did not reduce the yield of the tetrahydroindene diepoxide.

Example 2

Into a screw-top test tube were weighed out 0.50 g of apatite that is a solid catalyst support and 0.085 g (0.015 mmol) of $(Cety1Py)_9(NH_4)[H_2W_{12}O_{42}]$ that is a solid catalyst, followed by well-mixing. To the mixture were added 0.60 g (5.0 mmol) of tetrahydroindene, 0.31 g of toluene and 0.87 g (9.0 mmol) of a 35% hydrogen peroxide. After the mixture was stirred at 20° C. for 6 hours, the resulting reaction mixture was extracted with toluene (1 mL×3 times). The solvent was distilled out from the extracted solution thereby producing a crude product. The crude product was fed into a distillation still and distilled at a pressure of 2 mmHg thereby producing 0.40 g of tetrahydroindene diepoxide as a fraction at a column top temperature of 90° C. The yield of the product (diepoxide yield) was 53%. As the residue resulting from the extraction, 0.56 g of a solid catalyst support and solid catalyst mixture was produced.

$(Cety1Py)_9(NH_4)[H_2W_{12}O_{42}]$ that is a solid catalyst was weighed out in an amount of 0.028 g (0.0050 mmol) and then well-mixed with 0.56 g of the extract residue. To the mixture were added 0.60 g (5.0 mmol) of tetrahydroindene and 0.87 g (9.0 mmol) of a 35% hydrogen peroxide solution. After the mixture was stirred at 20° C. for 6 hours, the reaction mixture was extracted with toluene (1 mL×3 times). The solvent was distilled out from the extracted solution thereby producing a crude product. The crude product was fed into a distillation still and distilled at a pressure of 2 mmHg thereby producing 0.43 g of tetrahydroindene diepoxide as a fraction at a column top temperature of 90° C. The yield of the product (diepoxide yield) was 56%. Repeated use of the extract residue that is a solid catalyst support and solid catalyst mixture in the same manner did not reduce the yield of the tetrahydroindene diepoxide.

Comparative Example 1

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.60 g (5.0 mmol) of tetrahydroindene and 0.87 g (9.0 mmol) of a 35% hydrogen peroxide. After the mixture was stirred at 20° C. for 6 hours, the resulting reaction mixture was extracted with toluene (1 mL×3 times). The solvent was distilled out from the extracted solution thereby producing a crude product. The crude product was fed into a distillation still and distilled at a pressure of 2 mmHg thereby producing 0.43 g of tetrahydroindene diepoxide as a fraction at a column top temperature of 90° C. The yield of the product (diepoxide yield) was 57%. As the residue resulting from extraction, 0.56 g of a solid catalyst support and solid catalyst mixture was produced.

To 0.56 g of the extract residue were added 0.57 g (4.8 mmol) of tetrahydroindene and 0.83 g (8.6 mmol) of a 35% hydrogen peroxide. After the mixture was stirred at 20° C. for 6 hours, the reaction mixture was extracted with toluene (1 mL×3 times). The solvent was distilled out from the extracted solution thereby producing a crude product. The crude product was fed into a distillation still and distilled at a pressure of 2 mmHg thereby producing 0.094 g of tetrahydroindene diepoxide as a fraction at a column top temperature of 90° C. The yield of the product (diepoxide yield) was 13%.

INDUSTRIAL APPLICABILITY

The method of the present invention can produce an epoxy compound at a higher reaction rate and yield.

The invention claimed is:

1. A method for producing an epoxy compound by reacting a compound having a carbon-carbon double bond with hydrogen peroxide, comprising carrying out repeatedly or continuously the following steps (1), (2) and (3):
    step (1) of reacting a compound having a carbon-carbon double bond with hydrogen peroxide in the coexistence of (a) the compound having a compound having a carbon-carbon double bond, (b) a hydrogen peroxide solution, (c) a powdered solid catalyst support and (d) a powdered solid catalyst and optionally further (e) an organic solvent to produce an epoxy compound;
    step (2) of separating the epoxy compound that is the reaction product from the reaction mixture produced in step 1; and
    step (3) of adding (d) the powdered solid catalyst and also adding (a) the compound having a carbon-carbon double bond, (b) the hydrogen peroxide solution, (c) the powdered solid catalyst support and optionally further (e) the organic solvent to the mixture of the powdered solid catalyst support and powdered solid catalyst after separating the reaction product in step (2)
    wherein the powdered solid catalyst is selected from the group consisting of isopolytungstic acids containing cetyltrimethylammonium as a cation and isopolytungstic acids containing $(NH_4)[H_7W_{12}O_{42}]$ and an organic cation selected from the group consisting of tetrabutylammonium, butylammonium, benzyltrimethylammonium, and cetylpyridinium.

2. The method for producing an epoxy compound according to claim 1 wherein the amount of the powdered solid catalyst added in step (3) is 1 percent by mass or more and 20 percent by mass of less on the basis of the mass of the compound having a carbon-carbon double bund added in step (3).

3. The method for producing an epoxy compound according to claim 1 wherein the total mass of the powdered solid catalyst and the powdered solid catalyst support is 100 percent by mass or less on the basis of the total mass of the compound having a carbon-carbon double bund and the hydrogen peroxide solution.

4. The method for producing an epoxy compound according to claim 1 wherein the organic solvent is selected from the group consisting of aliphatic hydrocarbons, aromatic hydrocarbons, alcohols, ethers, amides, ketones, nitriles, sulfones, epoxides and mixtures thereof.

5. The method for producing an epoxy compound according to claim 1 wherein the amount of the organic solvent is from 0 to 500 percent by mass on the basis of the compound having a carbon-carbon double bond.

6. The method for producing an epoxy compound according to claim 1 wherein the solid catalyst support is selected from the group consisting of phosphates, diatomaceous earth, silica, alumina, kaolin, silica-alumina and calcium fluoride.

7. The method for producing an epoxy compound according to claim 1 wherein the solid catalyst support is apatite.

8. The method for producing an epoxy compound according to claim 1 wherein the epoxy compound is a compound represented by formula (1) below:

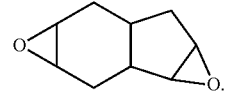

(1)

9. The method for producing an epoxy compound according to claim 1 wherein the powdered solid catalyst is $(CetylNMe_3)_7(NH_4)_3[H_2W_{12}O_{42}]$ or $(CetylNMe_3)_{10}[H_2W_{12}O_{42}]$.

10. The method for producing an epoxy compound according to claim 1 wherein the powdered solid catalyst is $(CetylPy)_9(NH_4)[H_2W_{12}O_{42}]$.

* * * * *